(12) United States Patent
Kieft

(10) Patent No.: US 10,039,518 B2
(45) Date of Patent: Aug. 7, 2018

(54) ROI PAINTING

(71) Applicant: KONINKLIJKE PHILIPS N.V., Eindhoven (NL)

(72) Inventor: Erik Rene Kieft, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 48 days.

(21) Appl. No.: 14/430,964

(22) PCT Filed: Sep. 27, 2013

(86) PCT No.: PCT/IB2013/058914
§ 371 (c)(1),
(2) Date: Mar. 25, 2015

(87) PCT Pub. No.: WO2014/053970
PCT Pub. Date: Apr. 10, 2014

(65) Prior Publication Data
US 2015/0272531 A1    Oct. 1, 2015

Related U.S. Application Data

(60) Provisional application No. 61/710,159, filed on Oct. 5, 2012.

(51) Int. Cl.
*A61B 6/06* (2006.01)
*A61B 6/12* (2006.01)
(Continued)

(52) U.S. Cl.
CPC ................ *A61B 6/547* (2013.01); *A61B 6/06* (2013.01); *A61B 6/12* (2013.01); *G06K 9/00912* (2013.01);
(Continued)

(58) Field of Classification Search
CPC .... A61B 6/00; A61B 6/02; A61B 6/04; A61B 6/06; A61B 6/12; A61B 6/48;
(Continued)

(56) References Cited

U.S. PATENT DOCUMENTS 7,340,033 B2    3/2008  Mollus
7,340,108 B2    3/2008  Florent et al.
(Continued)

FOREIGN PATENT DOCUMENTS

JP    2012061307 A    1/2007
JP    2011004966 A    1/2011
(Continued)

OTHER PUBLICATIONS

Baert, S.A.M. et al. "Guide Wire Tracking During Endovascular Interventions", MICCAI 2000, pp. 727-734, Springer-Verlag Berlin Heidelberg.

*Primary Examiner* — Anastasia Midkiff

(57) ABSTRACT

An apparatus and a method are provided for controlling collimation operation of a collimator in an x-ray imager during an intervention carried out by an operator. A first medical device is made to progress through a patient in an exploratory phase of the intervention. A path is recorded in a scout image formed from footprints of the first device as recorded in a sequence of projection images acquired by imager during the exploratory phase. Apparatus uses the path in the scout image to control collimation of the x-ray beam during a subsequent delivery phase where a second medical is made to progress through patient, said second device following the first device substantially along the same path.

12 Claims, 4 Drawing Sheets

(51) Int. Cl.
*G06T 7/00* (2017.01)
*A61B 6/00* (2006.01)
*G06K 9/00* (2006.01)
*G06T 1/00* (2006.01)

(52) U.S. Cl.
CPC ......... *G06T 1/0014* (2013.01); *G06T 7/0016* (2013.01); *A61B 6/4441* (2013.01); *A61B 6/487* (2013.01); *A61B 6/488* (2013.01); *A61B 6/5235* (2013.01); *A61B 6/54* (2013.01); *A61B 6/542* (2013.01); *A61B 2560/063* (2013.01)

(58) Field of Classification Search
CPC ......... A61B 6/486; A61B 6/487; A61B 6/504; A61B 6/52; A61B 6/5211; A61B 6/5217; A61B 6/5229; A61B 6/5235; A61B 6/54; A61B 6/542; A61B 6/547; A61B 2576/00; A61B 2560/00; A61B 2560/02; A61B 2560/04; A61B 2560/06; A61B 2560/063; A61B 2560/066; G01T 1/00; G01T 1/16; G01T 1/161; G06K 9/00496; G06K 9/00503; G06K 9/00523; G06K 9/00885; G06K 9/00912; G06T 1/00; G06T 1/0007; G06T 1/0014; G06T 5/00; G06T 5/10; G06T 7/00; G06T 7/0012; G06T 7/0014; G06T 7/0016; G06T 7/0022; G06T 7/0024; G06T 7/0028; G06T 7/003; G06T 7/004; G06T 7/0042; G06T 7/0044; G06T 7/20; G06T 7/2033; G06T 7/204; G21K 1/00; G21K 1/02; G21K 1/04
See application file for complete search history.

(56) References Cited

U.S. PATENT DOCUMENTS

| | | | |
|---|---|---|---|
| 7,778,688 | B2 | 8/2010 | Strommer |
| 8,165,660 | B2 | 4/2012 | Pfister et al. |
| 8,891,843 | B2 | 11/2014 | Ohishi |
| 9,280,837 | B2 | 3/2016 | Grass et al. |
| 9,492,103 | B2 | 11/2016 | Strommer et al. |
| 2004/0127789 | A1* | 7/2004 | Ogawa ............... A61B 6/481 600/425 |
| 2007/0197905 | A1 | 8/2007 | Timinger et al. |
| 2009/0196473 | A1 | 8/2009 | Fujii et al. |
| 2010/0111389 | A1 | 5/2010 | Strobel et al. |
| 2010/0274120 | A1 | 10/2010 | Heuscher |
| 2011/0164724 | A1 | 7/2011 | Ohta et al. |
| 2011/0182492 | A1 | 7/2011 | Grass et al. |
| 2013/0343631 | A1 | 12/2013 | Florent et al. |
| 2013/0344631 | A1 | 12/2013 | Florent et al. |

FOREIGN PATENT DOCUMENTS

| | | | | |
|---|---|---|---|---|
| WO | WO 2009083851 | A1 * | 7/2009 | ............. A61B 6/032 |
| WO | WO 2012123850 | A1 * | 9/2012 | ............... A61B 6/06 |

* cited by examiner

ROI PAINTING

FIELD OF THE INVENTION

The present invention relates to an apparatus for controlling x-ray beam collimation, a method for controlling x-ray beam collimation, to an x-ray beam collimator, to an x-ray imaging system, to a computer program element and to a computer readable medium.

BACKGROUND OF THE INVENTION

Minimizing both staff and patient dose for a given clinical procedure is a competitive issue in interventional X-ray procedures such a PCI (percutaneous coronary interventions) or others. In "tight collimation" relevant regions of interest (ROIs) are automatically detected in a clinical image by a suitable programmed image processing algorithm to so define clinically relevant areas at any step of the procedure. The detected ROI may then be used to restrict X-ray beam exposure as much as possible to only the relevant ROI. In this way, Dose Area Product (DAP) rate may be reduced by minimizing the irradiated area.

U.S. Pat. No. 7,340,033 describes a type of automatic collimation.

However it has been observed at times that current automatic collimation schemes are inflicted by inaccuracies.

SUMMARY OF THE INVENTION

There may therefore be a need for an alternative apparatus for automatically or at least semi-automatically controlling operation of an x-ray collimator.

The object of the present invention is solved by the subject matter of the independent claims where further embodiments are incorporated in the dependent claims. It should be noted that the following described aspect of the invention equally apply to the method for controlling x-ray beam collimation, to the collimator, to the x-ray imager system, to the computer program element and to the computer readable medium.

According to a first aspect of the invention there is provided an apparatus for controlling x-ray beam collimation, comprising:

an input port configured to receive a scout projection image of a first device's path, said projection image formed from a sequence of projection images acquired during progression of said first device through a body, said device tracing out said path whilst progressing; and a collimation controller configured to use the scout image to control operation of an x-ray imager's collimator to acquire an x-ray image of the object, the collimator, when so controlled, collimating x-ray imager's x-ray beam according to the path recorded in the scout image whilst a second device progresses through the body to follow said first device.

According to one embodiment, the first (medical) device is a guidewire and the second (medical) device is a balloon catheter or a stent or similar that is made to slide along the first device in a medical intervention such as PCI or similar carried out on an animal or human patient. In other words, the apparatus as proposed herein uses the "path" of the guidewire in one phase of the intervention (exploratory phase) to define the clinical region of interest or collimation area (collimation window or collimator's field of view) in other, subsequent phase (delivery phase) of the intervention. The path may be defined by using footprints of the guidewire's tip portion as the tip portion has a well-defined appearance in projection images which makes image analysis algorithms for their detection robust and relatively easy to develop and maintain. Since the second or other devices will travel over substantially the same path that the guidewire tip has previously traveled, using the accumulated path of the guidewire tip for dynamically adjusting and updating the collimation window will be sufficient to keep all relevant areas in the image "open" for the remainder of the procedure and the overall radiation exposure the patient can still be kept low. The path as recorded in the scout image is used for tight collimation when tracking progression of the second device in the delivery phase. The collimation is "tight" in the sense that the collimation window is relatively tightly shaped to conform or follow the outlines and/or direction defined by the path in the scout image.

According to one embodiment said path is an accumulated path formed from instantaneous footprints (projection views) of the first device as recorded by the sequence of projection images. According to one embodiment the path includes the shifted footprint positions of the first device that are due to cardiac and/or respiratory activity of the patient. The path is therefore broader than the actual path of the first device as it progresses through the vessel and is more like a "swath" swept out by the different instantaneous footprints because of the imparted motion due to the cardiac and/or respiratory activity. The path therefore "automatically" includes a safety margin so as to increase the likelihood that the second device is in the collimator's field of view when the collimator window is adjusted according to the path in the scout image. However in other embodiments is path is corrected for the cardiac and/or respiratory activity and a pre-defined safety margin to the path's left and/or right border and/or one or both of the path's end portions can be added.

According to one embodiment the apparatus includes a filter to filter the received scout image to smoothen out edges of said path's footprint in the scout image. This further enhances robustness of the proposed collimation control operation.

By harnessing for x-ray beam collimation of the second device the path of the first device affords low maintenance costs: A vast variety of (guidewire deployed) second devices with different shapes are used these days in coronary/vascular interventions. The proposed apparatus can be used with any of these without reprogramming collimation algorithms to detect their respective footprints in projection images because it is only the shape of the guidewire (first device) that needs to be detected for example in a sequence of fluoroscopic projection images ("fluoros") acquired during navigation of the guidewire. The path is then only formed from the guidewire footprints and the guidewire is substantially the same or at least very similar no matter what kind of second device is made to slide on the guidewire during delivery phase. It is only the information in the recorded path that is then used to automatically control and adjust collimator's collimation window to track the second device. In fact no segmentation in respect of the second device is needed once the path has been detected/segmented. No prior knowledge of the shape of the second devices is required. The apparatus is therefore capable to automatically control collimation operation even for devices by different manufacturers of for device newly introduced into the market. No rework of the detection algorithm is required or the rework is straightforward or minimal if, for example, guidewires of different thickness are to be used. In other words the proposed apparatus is robust in respect of the second devices' variations in shape and type.

According to one embodiment the apparatus includes an image accumulator or composer configured to previously form said scout image from the sequence of projection images. The scout image is formed in one embodiment by reading in a sequence of fluoros and segmenting for the instantaneous guidewire tip footprints. This is done in the exploratory phase which is previous to the follow-up delivery phase when the second device slides along the introduced guidewire whose tip by then has reached the final, target ROI (lesioned site) in the patient's body. In this embodiment there is single scout image in which the complete guidewire tip path has been recorded. In an alternative embodiment, there is a sequence of scout images each recoding a partial path with only the last scout image recording the complete path. In this embodiment the two phases may overlap so the both devices are resident in the body and neither has reached the target ROI yet. In this embodiment the image composer keeps recording the later ones of the scout images in the sequence whereas collimator takes turns in collimating in respect of the second device by using the earlier ones of the scout images from the sequence. Collimation in respect of the second device can then successively switch over to more recent once of the scout images as they are recorded.

According to one embodiment the controller is switchable to collimate the x-ray beam according to a footprint of the second device (BCF) in a live image acquired by the x-ray imager. In other words, the apparatus allows automatically or manually switching between live and cumulative tracking/collimation of the first device and of the second device. A live image is a fluoro where collimation is according to a footprint of the second or first device segmented/detected in a further fluoro acquired substantially immediately before acquisition of the later fluoro. A certain safety margin is added to ensure the device of interest is within the so obtained collimation window.

According to one embodiment, the controller, when controlling the collimator according to the second device's footprint and when no footprint of the second device is detected in a subsequent live image, the controller configured to then revert controlling the collimator according to the scout image so the collimation window is again or instead adjusted according to the scout image and not according to the footprint of the second device. This allows maintaining low dosage and fast operation in out-of-view scenarios. Completely retracting the collimator's blades to maximize the collimator window ("open" the collimator) is not necessary.

According to one embodiment the apparatus controller's control operation is adapted upon detection of a movement of the object or is adapted upon detection of a re-alignment of imager's x-ray source. In one embodiment the collimation according to the scout image is switched off and apparatus starts over to record a new scout image in respect of the newly assumed imager geometry, in particular the newly assumed position of the x-ray source.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
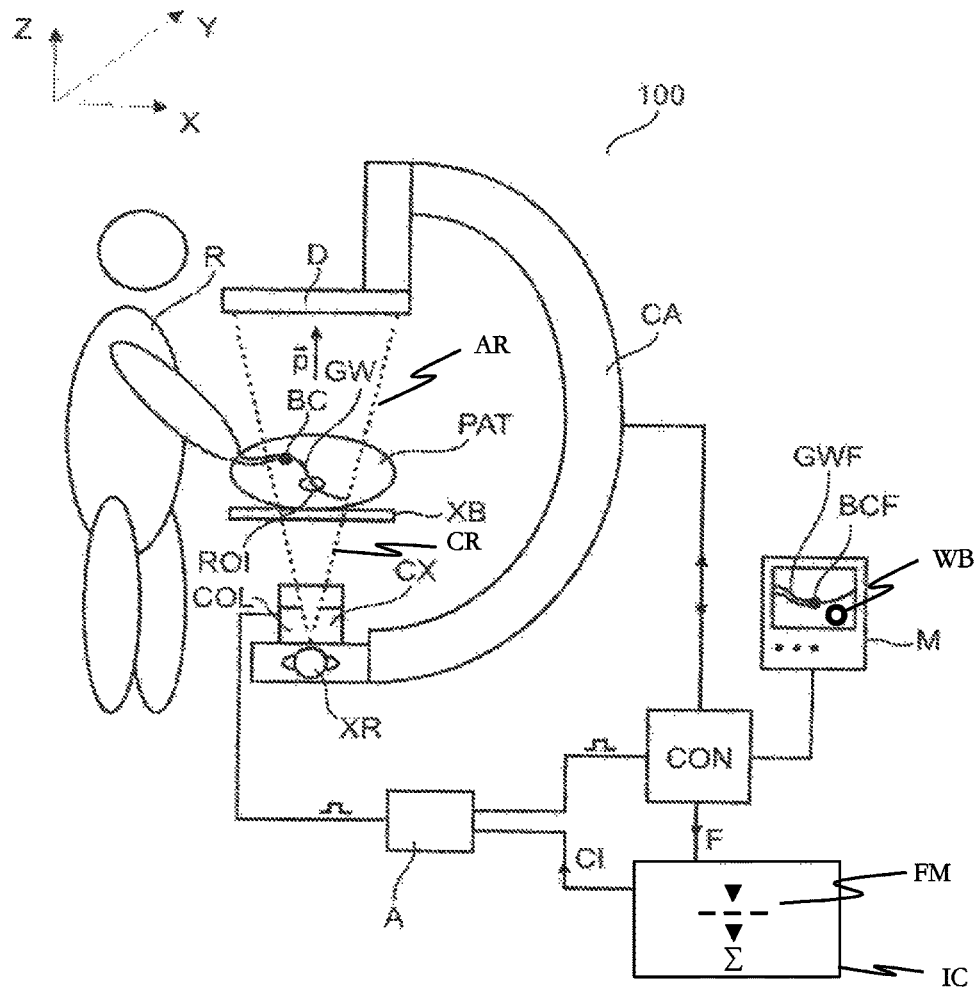
FIG. 1 shows an imaging device arrangement for use in an intervention.

With reference to FIG. 1 there is shown an x-ray imaging arrangement 100 that may be used by an interventional radiologist to support an intervention.

During the intervention a patient PAT is lying on an examination table XB such that the x-ray beam emitted by x-ray source passes through the region of interest, that is, the x-ray beam generated by x-ray source XR irradiates the one or more clinically relevant ROIs. Examples for such an intervention includes PCI's (percutaneous coronary interventions) carried out by an interventional radiologist R hereinafter referred to simply as the operator or user.

What is clinically relevant differs between different application fields. In coronary and (other) vascular applications, the interventional radiologist typically first gains access to the treatment area (target ROI) by navigating a guidewire GW to the target area. During this navigation phase, the respective ROIs at any one time may be defined and identified by the tip portion of guidewire GW. In subsequent phases of the procedure, other devices are moved along the path of the guidewire to the target treatment area ROI. Depending on the type of intervention, various types of devices can be used. Examples are catheters for deployment of stents, ballooning catheters, catheters for coiling of cerebral aneurysms or for gluing of arterio-venous malformations (AVMs) in patent's brain. In these subsequent phases, the ROI may be defined by positions of those subsequently introduced devices, possibly in combination with the guidewire if it is still present, and/or the coils/glue/stents to be deployed.

In other words, PCI and similar interventional procedures proceed in general in two phases one phase before the other. In the first, exploratory or navigation phase the guidewire GW or other medical device is used to access patients PATS coronary or peripheral vascular system, that is the target ROI. The initial guide-wire also called an X-wire is first inserted through body passage ways of patient's PAT to the lesion site where a medical procedural treatment is to take place. In a second phase, called the delivery or launch phase, occurring after said previous exploratory phase another medical device such as a catheter BC is advanced along and over the inserted guide-wire as to enable the catheter to follow the pathway predefined by the positioned guidewire GW to the point of treatment or target ROI. In possibly further steps, yet more devices or fluids may be inserted or delivered via the catheter tubing as needed. Guidewire GW is normally advanced beyond the target ROI for example a stenosed vessel area to allow the balloon catheter BC and or stents to treat the area and to be deployed there.

In both the exploratory phase and the delivery launch phase progression of the respective devices, that is, the guidewire GW and the balloon catheter BC, is monitored by acquisition of a sequence of fluoroscopy frames F as the respective devices GW or BC progress through the patient's passage ways.

Imager 100 includes a rigid C-arm CA having affixed thereto at one of its ends a detector D and to the other a housing CX which houses an x-ray tube XR and a collimator COL (hereinafter together referred to as the C-X-assembly). X-ray tube XR operates to generate and emit a primary radiation x-ray beam PR whose main direction is schematically indicted by vector p. As will be explained in more detail below with reference to FIG. 2, collimator COL operates to collimate said x-ray beam.

The C-arm construction allows the radiologist R to stay very close to the patient PAT at virtually any desired position around the patient called for by medical necessity whilst carrying out the intervention and whilst the projection images are acquired. The position of the arm CA is adjustable so that the projection images can be acquired along different projection directions p. The arm CA is rotatably mounted around the examination table XB. The arm CA and with it the CX assembly is driven by a stepper motor or other suitable actuator.

Overall operation of imager 100 is controlled by operator from a computer console CON. Console CON is coupled to screen M. Operator can control via said console OC any one image acquisition by releasing individual x-ray exposures for example by actuating a joy stick or pedal or other suitable input means coupled to said console CON.

During the intervention and imaging examination table XB (and with it patient PAT) is positioned between detector D and x-ray tube XR and collimator COL such that the lesioned site or any other related region of interest ROI is irradiated by collimated radiation beam CR.

Broadly, during an image acquisition the preliminary x-ray beam PR emanates from x-ray tube XR, is collimated by collimator COL to form collimated x-ray beam CR, which passes through patient PAT at said region ROI, experiences attenuation by interaction with matter therein, and the so attenuated beam AR then strikes detector D's surface at a plurality of the detector cells. Each cell that is struck by an individual ray (of said attenuated beam AR) responds by issuing a corresponding electric signal. The collection of said signals is then translated by a data acquisition system ("DAS"—not shown) into a respective digital value representative of said attenuation. The density of the organic material making up the ROI, for example rib cage and cardiac tissue in case of a PCI, determines the level of attenuation. High density material (such as bone) causes higher attenuation than less dense materials (such as the cardiac tissue). The collection of the so registered digital values for each (x-)ray are then consolidated into an array of digital values forming an X-ray projection image for a given acquisition time and projection direction.

Now, in order to acquire the x-ray image, the imager 100 needs first to be aligned to said region of interest ROI by adjusting c-arm CA position relative to patient PAT and by adjusting table XB height. This defines the imager's geometry. Other than rotating C-arm CA to change the imager's geometry, imager 100 also includes in some embodiments a panning functionality that allows shifting table XB (and hence patient PAT) in two dimensions.

Prior to the actual image acquisition, primary beam radiation PR is collimated to the desired ROI. This is achieved by Collimator COL when properly adjusted. Primary x-ray radiation PR generated by x-ray tube XR egresses same, then ingresses collimator COL and then egresses as a collimated primary radiation beam CR whose cross section is shown as a dashed-lined triangle in FIG. 1. It is understood that the shape of the beams' horizontal cross-section (formed by a horizontal plane thought to intersect said beam) is a matter of the collimator's construction and could be rectangular (as it indeed is according to the embodiment of FIG. 2) or circular or any other curvilinear shape. An objective in collimation is to adapt primary radiation beam PR's horizontal cross-section to the outlines of the region of interest ROI. Prior to collimator interaction, primary x-ray beam PR egressing x-ray tube XR (in projection direction p) is a divergent beam so in absence of collimator COL the cross-sectional dimensions of the beam p when reaching patient PAT would be much larger than the area of the desired ROI. This is unsatisfactory because patient dosage may have to be increased unnecessarily which in turn causes even more Compton scatter to occur. The purpose of collimator COL or "beam restrictor" is to restrict dimensions of the cross section of the beam CR so as to match in size and shape the beam CR's cross section to that of the region of interest ROI.

Figure 2:
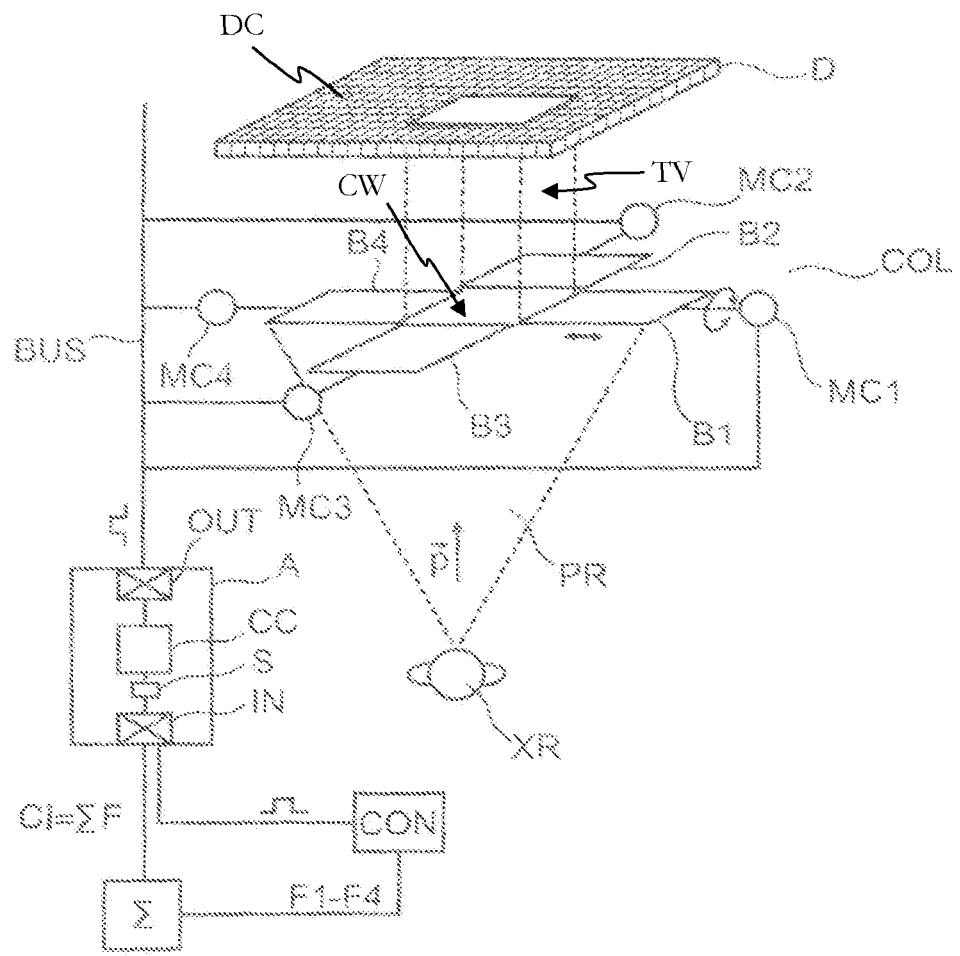
FIG. 2 shows a collimator and a control apparatus for controlling same as used in the arrangement of FIG. 1.

With reference to FIG. 2 an embodiment of collimator COL is shown in cut away view where the detector D's surface and detector cells DC are visible from above in a direction opposite to x-ray beam direction of travel p.

Collimator COL comprises two pairs of blades B1-4 or sheets ("shutters") formed from lead or tungsten or other highly radiation-opaque material. One pair is arranged perpendicularly to the other and the blades are individually addressable and movable by a respective collimator stepper motor MC1-4 so as to restrict more or less the beam in either or two of the two dimensions depending on their relative position. Blades B1-4 may be rotatable and/or shiftable in and out towards a center formed by the four blades as shown by curved and straight arrows for exemplary blade B1. In this way the collimated beam CR's cross section can be shaped to match the expected two dimensional outline of the region of interest ROI. The collimator arrangement in FIG. 2 allows shaping the beam into square or rectangular forms in various sizes. In another embodiment a multi-leaf collimator is used comprising instead of the four blades a large number of motor-movable slats or strips arranged in opposing relationship. A multi-leaf collimator allows forming more detailed or curvilinear shapes.

Setting up the collimator COL amounts to determine how to position the blades so as to make the resulting beam cross section match the perimeter of the ROI as close as possible ("tight collimation"). In the four blade collimator embodiment, the matching of said rectangular shape to the ROI is achieved by determining blade positions for each blade B1-4. When the blades are energized to assume the determined positions they together define an aperture or collimation window with which the smallest or a reasonably small rectangular beam cross section can be realized that still includes all of the desired ROI.

In one embodiment collimator COL additionally includes movable "wedges" (not shown) made from brass sheet or other non-radiation-opaque material that can be slid into position also to further restrict the aperture formed by the blades B1-4. Said wedges are likewise movable by stepper motors. Interposing said wedges make part of collimated beam CR impact patient PAT at lesser intensity than the remaining part of collimated beam CR. The respective sheets from which the wedges are formed have a vertical thickness that decreases from its center to its edges. Sliding in the wedges allows smoothing the radiation intensity drop around the apertures edge. Because of the gradually decreasing thickness, the degree of said smoothing can be fine-tuned by gradually moving wedges into position.

Operation of said stepper motors MC1-4 for blades or wedges is controlled by a control apparatus A issuing corresponding control signals to position each of the blades or wedges according to manually or automatically set collimator setting parameters. Apparatus A runs suitable driver software and includes suitable interface units to interface with collimator COL.

Each collimator setting or configuration corresponds to a specific position of blades B1-4 or wedges forming the collimator aperture shown in FIG. 2 bounded the four blades. Because of the high radiation opacity of blades B1-4, primary radiation beam PR incident on the blades B1-4 is blocked whereas that part of primary radiation beam PR that is directed at the aperture is not blocked so can pass collimator COL as collimated radiation beam CR to irradiate patient PAT volume in a target volume TV. The sequences of fluoros F obtained in the exploratory or the launch phase are also called "live images" as they are capable of showing at a given instant the position of the guide-wire GW and/or the balloon catheter BC. In order for the fluoros F to really show the respective positional footprints as shown in FIG. 1, collimator settings need be adjusted to restrict the x-ray beam on the respective relevant position where a certain part of the guidewire, for example its tip, resides at any given instant. In the following the term ROI is a context dependent term and is meant to include the relevant tip position of the guidewire GW at any given instant. In other words the ROI changes as guidewire GW progresses from entry point into the patient's body until arrival at the target ROI which is the lesioned site. For example, in PCI the operator when navigating guidewire GW must successfully negotiate a number of bifurcations or shunts in patient PAT's cardiac vasculature to eventually arrive at the target ROI. Each shunt along the way forms then an instant ROI.

Broadly speaking, a control apparatus A controls collimator COL over the course of time so as to ensure that the x-ray beam is always limited to the relevant ROI at any given time. The control apparatus A as proposed herein uses the path of the guidewire GW as traced out during the previous exploratory phase to define the relevant ROI's or collimation areas in the subsequent delivery launch phase of the second device BC. The path is obtained by combining footprints GWF the guidewire tip positions as recorded in the sequence of fluoros F acquired during the exploratory phase, that is, upon introduction into the patient of guidewire GW and once the lesioned site or target ROI has been reached. In yet other words a "scout" image CI is produced by an image composer IC during navigation in the exploratory phase of guidewire GW. Operation of control apparatus A will now be explained in more detail.

Apparatus A includes input port IN, output port OUT, a segmenter S and a collimator controller CC.

Apparatus A is switchable by operator R between two modes, a "live mode" and "cumulative mode". In each mode collimator COL control is different as will now be explained in detail.

During exploratory phase and when in live mode, an initial fluoro F is acquired by imager 100 either automatically or operator-triggered at a desired projection direction p with an initial collimator setting. The initial collimator setting defines an initial collimation window or field or view. Fluoro F is then received at console CON. Console CON then forwards said fluoro F to segmenter S. Segmenter S operates to read in said fluoro F and uses a segmenter to detect in fluoro F guide-wire GW's footprint, in particular footprint of guidewire GW's tip. Operation of segmenter is based on pixel grey-value thresholding. Spatial footprint information of detected footprint is then established. Spatial footprint information includes position and/or shape and/or area size of said footprint relative to detector D's image plane. Collimator controller CC then translates the received spatial footprint information into position data for the blades B1-B4 that would afford collimation window that is as small as possible and still includes substantially all (or a user-definable or automatic selection to discard poor segmentations) of the detected guidewire tip footprints GWF and/or includes the tip footprints GWF plus a user-definable margin circumscribing the tip footprints GWF. Based on the blade position data, Collimator controller CC then issues control signals for collimator COL and forwards same to actuators MC1-4 via a bus system BUS. Blades B1-B4 are then energized by actuators MC1-4 to assume the computed position. The so updated collimator setting can then be used for a subsequent fluoro acquisition to thereby collimate X-ray beam relatively tightly around the current ROI defined by the current guidewire tip position. The above guidewire tip segmentation operation is then repeated for any new fluoro that is subsequently acquired. The collimator window therefore is re-adjusted with each fluoro acquisition to follow the changing positions of the guidewire GW (tip) as it progresses through patient PAT towards the target ROI. In this manner, over the course of the exploratory phase a sequence of fluoros $F_i$ are received and the spatial footprint information encoded in the respective fluoros are used to control collimator COL.

As a background process, image composer IC operates to combine all of the detected guidewire tip footprints from the individual fluoros F into a combined or "scout" image CI which is then forwarded via input port IN to collimation controller CC. The scout image may be understood as an accumulated ROI and operation of composer IC may be understood as "ROI painting" so that all the relevant ROIs corresponding to the guidewire GW's changing positions are recorded as a path. According to one embodiment, the respective guidewire tip footprints GWF are combined only into a single scout image CI. The single scout image CI records the actual guidewire GW's tip path in its entirety throughout the guidewire GW's progression form the entry point to the target ROI. According to another embodiment, image composer IC produces a sequence of scout images $CI_i$, each one of the scout image including a partial path of the guidewire GW tip up to a certain instant, with the last scout image in the sequence recording the complete path. The single scout image CI or each of the scout images $CI_i$ are formed by superposing the individual guidewire GW tip footprints GWF (as detected in the respective one of the fluoros F) onto the same image. No registration is required when the sequence of fluoros F are acquired along the same projection direction. If different projection directions are used for different fluoros F in the sequence, the sequence of fluoros $F_i$ must be registered first so as to align same along a common coordinate system before superposing the respective footprints into the same image. To this effect, apparatus A includes a registration module that operates to connect with console CON when a change in the imager's geometry (for example a change in C-arm CA position) is registered and to then retrieve a current imager geometry. Alternatively, registration module reads out imager geometry data as recorded in the meta-data of each of the acquired fluoros. The current imager geometry is compared with the previous imager geometry to compute the registration.

When in cumulative collimation mode, collimator controller CC reads in said scout image CI and translates the coordinates of the total path as recorded in said combined image into corresponding control signals for each of the blades of collimator COL similar to "live mode" as explained earlier. In contrast to live mode however, operation of segmenter is not needed. Collimation window CW is adjusted to cover all or a selectable part of the previously recorded path so collimation in cumulative mode is not according to a tip footprint in the latest available fluoro as is the case for "live mode" but collimator's field of view is adjusted tightly around the total or partial path so that, in a subsequent image acquisition, collimated radiation CR irradiates that part of the patient that corresponds to the total or partial path and that primary radiation exposure to parts other than those corresponding to the path is minimized.

Figure 3:
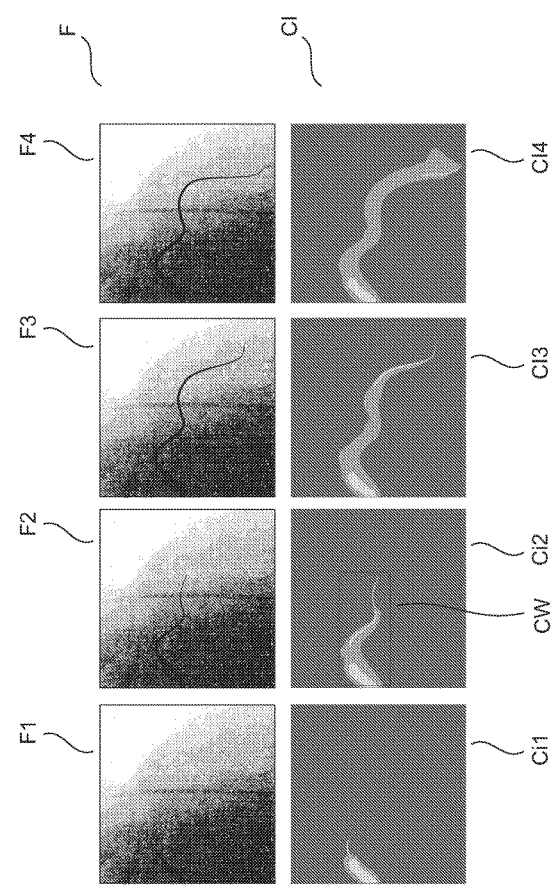
FIG. 3 shows a sequence of fluoroscopic images and a sequence of scout images.

With reference to the top row, left to right of FIG. 3 shows stills F1-F4 from a fluoroscopic run with the footprint GWF (shown in black) of the guidewire GW. The bottom row, from left to right of FIG. 3 shows corresponding scout images CI1-CI4 in grey combined with a live mask (shown in white) obtained from the live fluoros F1-4. FIG. 3 illustrates the gradual building up of the path. In this case the live mask consists of a combination of the guidewire tip and the tip of the guiding catheter at the left border of the image. Scout image $C_i$ in the sequence of scout images includes the guidewire tip positions GWF as detected in fluoros from F1 up to and including Fi. The next scout image $CI_{i+1}$ is then gotten by combining guidewire footprint GWF of the next fluoro $F_{i+1}$ with the previous scout image $CI_i$ and so on with the last scout image, in this case, CI4, including the complete path of guidewire GW. According to one embodiment console CON includes a graphic controller that effects on user demand display on screen M of the images shown in the lower row of FIG. 3. In other words, graphics controller generates images by overlaying in a selected one of the scout images CI a current one of the live fluoros as shown in FIG. 3. An exemplary "tight" rectangular collimation window CW is shown for scout image CI2.

Collimation control according to any one of the scout images CI, that is, cumulative collimation mode, is preferably used by controller CC in the delivery or launch phase when balloon catheter BC is introduced to slide along guidewire GW. In embodiments where there is more than one scout image as shown above in FIG. 3, user R can switch between the different scout images. In one embodiment, the selection is semiautomatic. The user activates cumulative collimation mode upon introduction of the second device BC. Apparatus then selects the first scout image in the sequence, that is, the one in which the shortest path has been recorded. If, when acquiring the images during the delivery phase, the second device happens to be outside the current collimation window according to said first scout image, controller switches to collimation according to the second scout image and so on. In this manner progression of the balloon catheter BC along the guidewire can be tracked. Switching to the second or subsequent scout images for collimation control is preferably user R initiated upon actuation of a button displayed as a GUI widget WB on monitor M having a touchscreen functionality or by actuation of a physical button arranged on console CON or by actuation of a pedal.

According to one embodiment, operation of image composer IC to record or accumulate the ROIs defined by the collection of guidewire GW footprint is initiated automatically upon the first time a guidewire tip is detected in a given fluoro F. Operation of composer IC then continues throughout the remainder of the exploratory phase. In this scenario, ROI painting is always "on". Operator R does not need any special knowledge about when exactly navigation of the first device ends and navigation of the second device starts.

In one embodiment, switching from live collimation mode to cumulative ROI mode is up to user R and can be initiated by actuating a physical button arranged at console CON or by actuating a pedal in communication with apparatus A and or console CON or by actuating a GUI button widget displayed on screen M having a touchscreen functionality. According to one embodiment, collimation operates according to live mode during the guidewire navigation phase and is then manually switched by user R to cumulative mode for delivery phase (ballooning, stenting) of the intervention.

In one embodiment, cumulative collimation mode is used as an automatic fallback scenario for the live collimation mode. If the guidewire tip has been visible for some time into the exploratory phase during live mode, automatic collimation reverts to the cumulative collimation mode when the guidewire tip is temporarily not detected by segmenter for a given fluoro. This allows ensuring, for example in the PCI case described above, that relevant coronary branches are free for any other devices to appear. Furthermore completely retracting collimator blades to make available a maximum collimation window is not necessary when the GW tip is temporally out of view. Reverting to the cumulative collimation mode allows "finding" the guidewire tip with high likelihood and still keep radiation exposure of patient PAT low.

Apparatus A may also be used in in the context of multiple devices for example if the operator R starts navigating the second device BC while the first device GW is still visible, that is, is still in the navigation phase. In this multiple device context, operator R manually switches to cumulative collimation when navigation of second device BC commences and apparatus automatically switches over to cumulative collimation whenever segmenter S is unable to detect first device GW. In one variation of this embodiment, automatic live collimation is used only during navigation of the first device in the exploratory phase is then manually switched off during navigation of the second device BC.

According to one embodiment apparatus A is configured to compensate for table XB panning. A suitable detector detects patient table XB movement and the collimation window is shifted accordingly to so retain the same position relative to the patient PAT.

According to one embodiment apparatus A is configured to reset or switch off cumulative mode upon detection of a change in C-arm CA orientation.

According to one embodiment apparatus A is configured to apply different safety margins for the two collimation modes, live mode and cumulative mode. The path as recorded in the later scout images (obtained after a brief startup period) already includes all phases of periodic motion undergone by the organ in question. The safety margins are added to the edges of a detected ROI for safety and/or robustness. In 'live' collimation, especially the heart, these margins need to be relatively large because of cardiac activity. In 'cumulative' collimation, the different possible positions of the device as a result of cardiac motion are already included in the cumulative ROI. Therefore, there is not as much need for adding extra margins for robustness.

According to one embodiment, image composer IC includes a filter module FM with or without thresholding to form the accumulated ROI or path in the combined image CI. According to one embodiment, said filter is a convolution filter. This allows smoothing the outline of the accumulated ROI or path. Applying a threshold to the filtered ROI allows identifying and removing of "outliers".

The components of control apparatus A are shown as integrated in one single unit. However in alternative embodiments, some or all components are arranged as separate modules in a distributed architecture and connected in a suitable communication network. Controller CC and its components may be arranged as dedicated FPGAs or as hardwired standalone chips. In some embodiments, controller CC or some of it components are resident in work station CON running as software routines. The components may be programmed in a suitable scientific computing platform such as Matlab® or Simulink® and then translated into C++ or C routines maintained in a library and linked when called on by work station CON.

In some embodiments image composer IC is included as a component of apparatus A.

Figure 4:
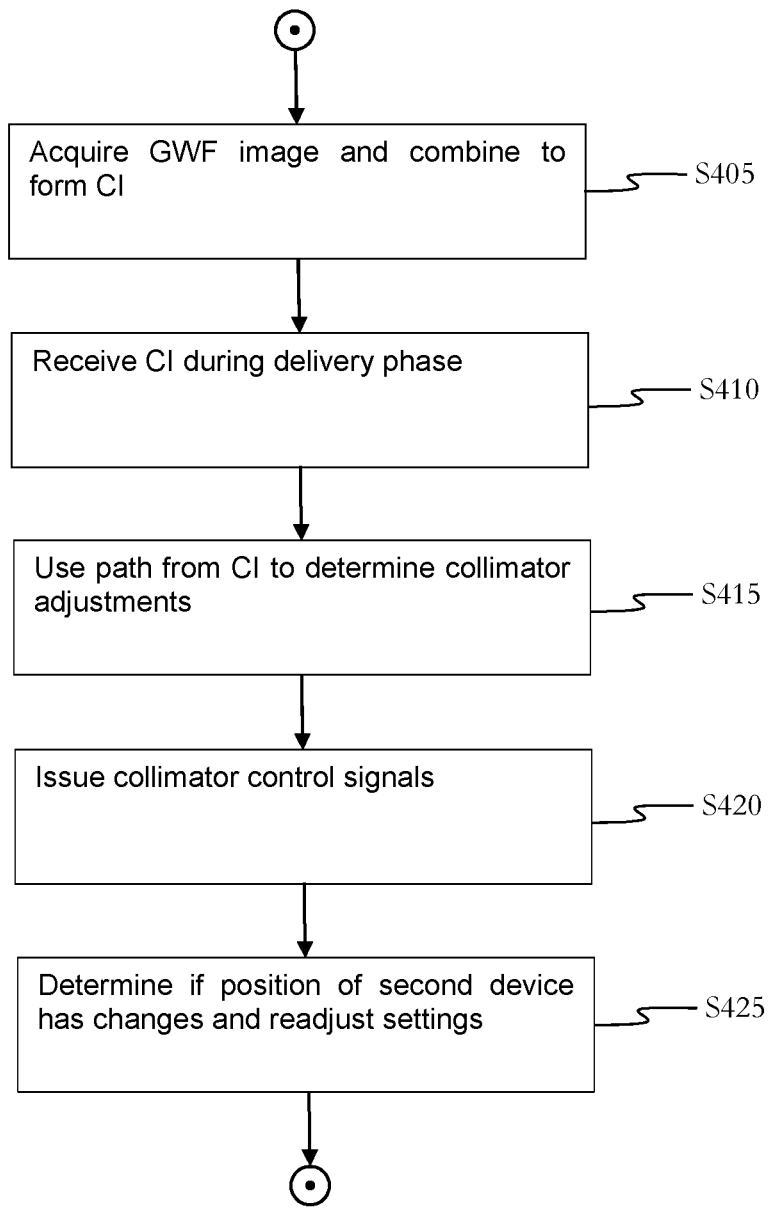
FIG. 4 shows a flow chart of a method of controlling a collimator.

With reference to FIG. 4 a flow chart for a method of controlling a collimator is shown.

At step S405 a sequence of previous fluoro images are acquired of a guidewire or similar device resident in a patient at different positions. Footprints of said device are detected and combined into a combined image CI. In other words, the combined image records a path traced out by the guidewire as it progresses from an entry point into patient to a lesioned site or target ROI in said patient.

In step 410 said combined image CI is received in a subsequent phase where a second device is likewise delivered to the lesioned site whilst sliding on or over the first device.

In step S415 position information for the path as recorded in the combined image is used to control and adjust a collimator's aperture or collimation window to direct or restrict an x-ray beam to or on a patient area that corresponds to the path. The path position information includes shape and size of the recorded path.

In step S420 control signals for the collimator are issued to the collimator to so instruct same to collimate the x-ray beam according to the path recorded in the combined image CI. In one embodiment there is a plurality or sequence of combined images. Each combined image of the plurality of combined includes a combination of footprints up to a certain instant so each combined image records only a partial path of the first device. A combined image further down the sequence includes the GW path up to later instance than a previous image in the sequence of combined images.

In an embodiment where a plurality of combined images are used to control collimator operation there is an optional step S425 in which it is determined whether the position of the second device has changed. If no, a collimation setting according to a current combined image is maintained. If however it is determined that the current position of the second device has changed a subsequent one of the combined images in the sequence is retrieved and is now used instead of the previous one to re-adjust the collimation setting of the collimator. In other words the collimator is successively controlled to collimate on a longer path up to the point where the entire path is covered.

The path recorded in each of the combined images is broader than the actual path of the first device. This broadening is due patient motion, for example cardiac or respiratory activity of the patient whilst the images were taken. The broadening of the path is not corrected but retained as a safety margin to so increase robustness of the proposed method.

Those schooled in the art will understand that application of above described apparatus is not restricted to the described guidewire/balloon catheter PCI scenario but can be applied for any interventions where multiple devices are used and where positions of one device holds clues for the position other devices. Furthermore using the tip portion of the guidewire GW to define the instantaneous ROIs is but one example. Other salient device portions may be used instead of tip portions.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an"

does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for controlling x-ray beam collimation, comprising:
    an input port configured to receive a scout projection image of a path of a first device, said projection image formed from a sequence of projection images acquired during progression of said first device through a body, said device tracing out said path whilst progressing;
    a collimation controller configured to use the scout image to control operation of a collimator of an x-ray imaging device, such that, when so controlled, the collimator limits an x-ray beam of the x-ray imaging device according to the path recorded in the scout image whilst a second device progresses through the body to follow said first device;
    wherein said path is an accumulated path formed from instantaneous footprints of the first device as recorded by the sequence of projection images.

2. The apparatus of claim 1, wherein the second device slides along the first device.

3. The apparatus of claim 1, further including a filter to filter the received scout image to smoothen out edges of said path's footprint in the scout image.

4. The apparatus of claim 1, further including an image accumulator configured to form said scout image from the sequence of projection images.

5. The apparatus of claim 1, wherein controller's control operation is adapted upon detection of a movement of the object by an appropriate sensor or is adapted upon detection of a re-alignment of an x-ray source of the imaging device.

6. The apparatus of claim 1, wherein the controller is switchable to collimate the x-ray beam according to a footprint of the second device in a live image acquired by the x-ray imaging device.

7. The apparatus of claim 6, wherein, when the controller is controlling the collimator according to the second device footprint and, when no footprint of the second device is detected in a subsequent live image, the controller is configured to revert to controlling the collimator according to the scout image.

8. A method of controlling x-ray beam collimation comprising the steps of:
    receiving a scout projection image of a first device's path, said projection image formed from a sequence of projection images acquired during progression of said first device through a body, said device tracing out said path whilst progressing;
    using the scout image to control operation of a collimator of an x-ray imaging device, such that, when so controlled, the collimator limits an x-ray beam of the x-ray imaging device according to the path recorded in the scout image to acquire a projection image whilst a second device progresses through the body to follow said first device;
    wherein said path is an accumulated path formed from instantaneous footprints of the first device as recorded by the sequence of projection images.

9. The method of claim 8, wherein the scout image is one of a sequence of scout images each including a portion of the path, the method further including the step of:
    switching, upon user request, from a current scout image to a later, second scout image and instead of using the current scout image for collimation control, using said later scout image for the collimation control.

10. An x-ray beam collimator including an apparatus of claim 1.

11. An x-ray imaging system including the collimator of claim 10.

12. A non-transient computer readable medium having stored thereon program code which, when executed by a computer causes a collimator of an x-ray imaging device to perform the steps of:
    receiving a scout projection image of a first device's path, said projection image formed from a sequence of projection images acquired during progression of said first device through a body, said device tracing out said path whilst progressing; and
    using the scout image to control operation of a collimator of an x-ray imaging device, such that when so controlled, the collimator limits an x-ray beam of the x-ray imaging device according to the path recorded in the scout image to acquire a projection image whilst a second device progresses through the body to follow said first device.

* * * * *